(12) United States Patent
Blake et al.

(10) Patent No.: US 10,151,413 B2
(45) Date of Patent: Dec. 11, 2018

(54) MODULAR FLUID CONNECTION ASSEMBLY

(71) Applicant: SARTORIUS STEDIM FMT SAS, Aubagne (FR)

(72) Inventors: Florian Blake, La Ciotat (FR); Jeremy Gibelin, Le Beausset (FR)

(73) Assignee: SATORIUS STEDIM FMT SAS, Aubagne (FR)

( * ) Notice: Subject to any disclaimer, the term of this patent is extended or adjusted under 35 U.S.C. 154(b) by 166 days.

(21) Appl. No.: 15/118,715

(22) PCT Filed: Feb. 11, 2015

(86) PCT No.: PCT/FR2015/050341
§ 371 (c)(1),
(2) Date: Aug. 12, 2016

(87) PCT Pub. No.: WO2015/121589
PCT Pub. Date: Aug. 20, 2015

(65) Prior Publication Data
US 2017/0045168 A1    Feb. 16, 2017

(30) Foreign Application Priority Data
Feb. 14, 2014  (FR) ...................................... 14 51187

(51) Int. Cl.
*F16L 37/084*    (2006.01)
(52) U.S. Cl.
CPC ................. *F16L 37/0841* (2013.01)
(58) Field of Classification Search
CPC ............................ F16L 37/0841; F16L 21/08
(Continued)

(56) References Cited

U.S. PATENT DOCUMENTS

| | | | | |
|---|---|---|---|---|
| 1,881,980 A | * | 10/1932 | Thomas, Jr. | .......... F16L 37/144 285/305 |
| 3,913,954 A | * | 10/1975 | Klimpl | .................. F16L 37/144 285/305 |

(Continued)

FOREIGN PATENT DOCUMENTS

| | | |
|---|---|---|
| DE | 92 08 976 U1 | 8/1992 |
| EP | 0 566 889 A1 | 10/1993 |
| WO | 2010/011883 A1 | 1/2010 |

OTHER PUBLICATIONS

International Search Report, dated Jun. 5, 2015, from corresponding International Application No. PCT/FR2015/050341.

*Primary Examiner* — Aaron M Dunwoody
(74) *Attorney, Agent, or Firm* — Young & Thompson

(57) ABSTRACT

A modular fluid connection assembly includes a female connector (1) for fluid connection, provided to receive a male connector (2) having an external annular retaining rim (24), the female connector including a body (10) with an axial bore X, and a slide forming a transverse housing (4), the housing (4) including two parallel lateral grooves (41, 42) and the housing opening at at least one of its ends (40) along the direction of the slide Z, the assembly including a non-unlocking locking element (3), in the form of a deformable locking ring (3), the assembly including an unlocking locking element (5), in the form of a locking slider (5), in which the female connector is configured to receive equally either a non-unlocking element, or an unlocking element.

20 Claims, 5 Drawing Sheets

(58) Field of Classification Search
USPC .................................. 285/80, 317, 305, 12
See application file for complete search history.

(56) References Cited

U.S. PATENT DOCUMENTS

| | | | | |
|---|---|---|---|---|
| 5,090,747 | A * | 2/1992 | Kotake | .................. F16B 21/16 |
| | | | | 285/305 |
| 5,378,024 | A | 1/1995 | Kumagai et al. | |
| 5,573,279 | A | 11/1996 | Rea et al. | |
| 5,782,502 | A * | 7/1998 | Lewis | .................. F16L 37/144 |
| | | | | 285/305 |
| 5,941,577 | A | 8/1999 | Musellec | |
| 6,231,089 | B1 * | 5/2001 | DeCler | ............... F16L 37/0841 |
| | | | | 285/308 |
| 7,845,684 | B2 * | 12/2010 | Gaudin | ............... F16L 37/0841 |
| | | | | 285/317 |
| 8,764,068 | B2 * | 7/2014 | Frick | ............... F16L 37/0841 |
| | | | | 285/308 |
| 2002/0093194 | A1 * | 7/2002 | Lacroix | ............... F16L 37/0841 |
| | | | | 285/80 |
| 2004/0189001 | A1 | 9/2004 | Poder | |
| 2005/0200125 | A1 * | 9/2005 | Andre | .................. F16L 37/144 |
| | | | | 285/305 |
| 2009/0167018 | A1 * | 7/2009 | Lien | ........................ F16L 37/38 |
| | | | | 285/308 |
| 2009/0250559 | A1 * | 10/2009 | Benoit | .................... F16L 5/027 |
| | | | | 248/49 |
| 2011/0210541 | A1 * | 9/2011 | Lewis | ................. F16L 37/0841 |
| | | | | 285/317 |
| 2013/0161941 | A1 * | 6/2013 | Zulauf | .................... F16L 21/08 |
| | | | | 285/80 |
| 2016/0076679 | A1 * | 3/2016 | Mendyk | ............... F16L 37/0841 |
| | | | | 285/81 |
| 2016/0252201 | A1 * | 9/2016 | Chintalapati | ....... F16L 37/0841 |
| | | | | 285/305 |
| 2017/0045169 | A1 * | 2/2017 | Gibelin | ............... F16L 37/0841 |
| 2017/0051859 | A1 * | 2/2017 | Blake | .................... F16B 21/186 |

* cited by examiner

MODULAR FLUID CONNECTION ASSEMBLY

TECHNICAL FIELD OF THE INVENTION

The invention relates to fluid connectors, in particular fluid connection assemblies that connect a female connector to a male connector for the purpose of connecting one fluid pipe to another pipe or to a container, in the field of biopharmaceutical applications.

BACKGROUND OF THE INVENTION

More specifically, flexible tubes or pipes, and recipients or containers, are used in the biopharmaceutical field to transport and contain various biopharmaceutical substances, usually with the necessary aseptic precautions. In the field of biopharmaceutical applications, fluids are transported and stored at low pressure, usually below 10 bar and most often below 2 bar, preferably at a pressure close to atmospheric pressure.

When using certain biopharmaceutical substances, it may be necessary to temporarily guarantee sufficiently sterile conditions after various components (pipes and/or containers) have been connected, while maintaining the possibility of uncoupling the connection when necessary.

In other cases of using biopharmaceutical substances, it may be necessary to guarantee conditions of complete sterility after various components (pipes and/or containers) have been connected. To this end, it is convenient to use male-female locking connections that cannot be detached after coupling, which ensures that no undesired uncoupling will break the sterile conditions.

This kind of connection needs to be obtained by a simple and quick coupling. In practice, solutions are preferred where the coupling is achieved by an axial translational movement without rotation to insert the male connector into the female connector.

To cover all possible cases, usually permanently attached connections are used as well as lockable connections with the possibility of unlocking.

Virtually tamperproof connections are known, for example from patents EP-A-0566889 and U.S. Pat. No. 5,573,279. Also known from patent WO2010/011883 are lockable connections with the possibility of unlocking.

However, the female connectors of these types of connection are quite different from each other, especially in their shape.

There is therefore a need to provide modular solutions which at least partially overcome the aforementioned disadvantage of the known prior art.

GENERAL DESCRIPTION OF THE INVENTION

According to a first aspect, the invention relates to an assembly (in other words a "kit") comprising a female connector for fluid connection, adapted for receiving a male connector having a retaining external annular rim, the female connector comprising a body with a bore of axis X, and a housing forming a slide (for example a slot) extending generally within a transverse plane YZ perpendicular to the axis, the housing comprising two parallel lateral grooves and the housing being open at least at one of its ends in the direction Z of the slide, the assembly (kit) comprising a non-unlockable locking element, in the form of a deformable locking ring formed as one piece and adapted to be inserted into the housing and to lock the male connector in the coupling position, with no possibility of unlocking by a user operation, the assembly (kit) comprising an unlockable locking element, in the form of a locking slider adapted to be inserted into the housing and movable between a first position referred to as the locking position and a second position referred to as the unlocking position, the locking slider comprising a locking plate with a central opening through which the male connector can pass, and an actuation pushbutton integrally formed with the plate, configured to be pushed toward the axis in order to unlock the connection, characterized in that the female connector is configured to receive indiscriminately either a non-unlockable element or an unlockable element.

A single definition for the female connector can thus be used to form either an unlockable connection or a non-unlockable connection. Thus, with only three elements, namely the connector, the deformable ring, and the slider, a modular assembly is formed that provides an unlockable female connector and a non-unlockable female connector adapted to receive a male connector. The female connector can thus first be assembled onto a flexible tube or reservoir, pouch or container, and then the desired locking element can be inserted in a later step. This allows preparing sub-assemblies earlier in the process, or even automated assembly operations for these components.

In one embodiment, the locking slider and the deformable ring are asymmetrical with respect to the transverse plane YZ, with the front side of the deformable ring and the front side of the locking slider respectively having a bevel shape. This facilitates insertion of the front portion of the male connector into the female connector and into the locking element inserted therein.

In one embodiment, the housing is asymmetrical with respect to the transverse plane YZ, the locking slider and the deformable ring each comprising at least one projecting pin designed to engage with at least one corresponding notch in the housing. The deformable ring or the locking slider can thus only be inserted one of two possible directions, meaning with front face/rear face foolproofing. In addition, this offers a simple and visual solution for proper manual or automated installation of the ring in the correct direction.

In one embodiment, the housing is open at both ends along Z and is symmetrical with respect to the XY plane, so that it is possible to insert the locking slider and the deformable ring indiscriminately from either side of the housing forming a slide. This arrangement increases the possibilities of automating the assembly.

In one embodiment, the locking slider has a double symmetry, with respect to planes XZ and YZ. Thus, if the shape of the ramp portions of the male connector so allows, a slide can be provided that can be inserted into the housing in either of the two possible directions (front/rear), with no need for foolproofing.

In one embodiment, the deformable ring has a triple symmetry, with respect to planes XZ, XY, and YZ; such that there is no risk of error when assembling the deformable ring inside the housing.

In one embodiment, the body of the female connector is made of a first biocompatible plastic material, the deformable ring is made of a second plastic material, and the locking slider is made of the second plastic material or of a third plastic material, such that the respective materials of the female connector and locking ring and locking slider can be optimized; in particular, a second plastic material (or third plastic material) can be chosen having a mechanical performance that optimizes the compromise between rigidity and elasticity. In addition, the respective optimization of the two materials allows manufacturing these components at particularly advantageous costs.

In one embodiment, the grooves of the housing comprise at least one recess configured to indiscriminately accommodate projections that are respectively part of either the deformable ring or the locking slider. This provides a very simple means for retaining the locking element inside the housing.

In one embodiment, the housing comprises recesses arranged in pairs, symmetrically with respect to the XY plane, so as to accommodate the deformable ring and/or the slider regardless of the end of the housing through which they are inserted. The deformable ring and/or the slider can thus be inserted from either side of the housing forming a slide, with the retaining means being identical regardless of the direction of insertion.

In one embodiment, the locking ring comprises two diametrically opposed first arched portions, concave as viewed from the axis, and two diametrically opposed second arched portions of inverse curvature, meaning convex as viewed from the axis, each of the second arched portions being interposed between two first arched portions; whereby a definitive locking is obtained after the male connector is locked in the female connector: it is no longer possible to unlock the connection by manipulation or pressure on the locking ring, as the second arched portions are not directly accessible and the second arched portions tend to reinforce the lock in case of applied force or impact.

In one embodiment, the locking slider comprises at least one flexible tab integrally formed with the slider, the flexible tab returning the slider toward the first position and able to flex to allow the plate to move toward the second position, the flexible tab being configured to press on each side of the mouth of the housing in the axial direction X, such that the return force is balanced along X and does not create torque that could jam the locking plate.

In one embodiment, the female connector may further comprise in its rear portion a tubular end piece for receiving and retaining a flexible tube; the female connector thus forms a modular interface for the flexible tube on which it is mounted.

In one embodiment, the female connector may further comprise in its rear portion an attachment flange configured to be sealingly fixed to the wall of a container or a pouch; the female connector thus forms a modular interface for the container or pouch on which it is mounted.

DESCRIPTION OF PREFERRED EMBODIMENTS OF THE INVENTION

Below is a detailed description of several embodiments of the invention with examples and with reference to the drawings.

Figure 1:
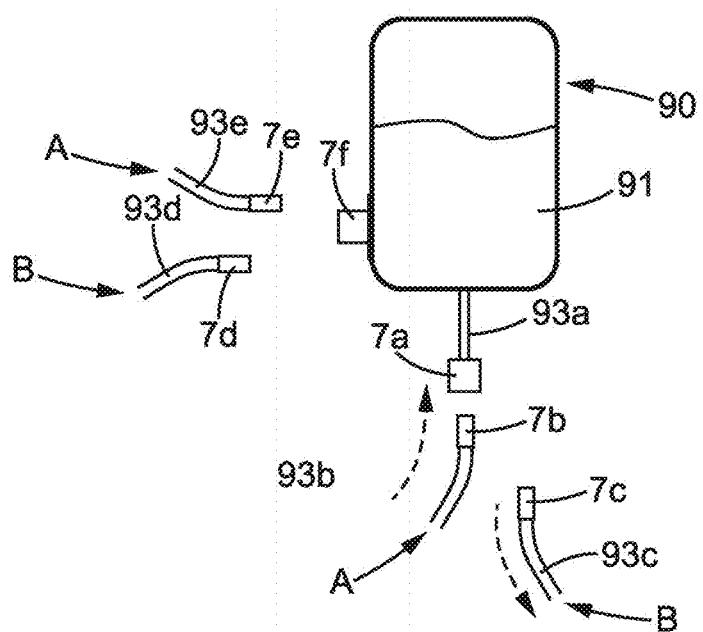
FIG. 1 schematically represents various components that may be used in a biopharmaceutical fluid system.

In FIG. 1, a pouch 90 containing biopharmaceutical material 91 is represented, the pouch forming a flexible, semi-rigid, or rigid container. In the process of preparing this pouch and using it as a container for biopharmaceutical substances, the pouch is filled with the desired substance, the pouch is possibly transported from a preparation site to a usage site, and it must be arranged so that the biopharmaceutical substance can be dispensed out of the pouch.

Note that the components used in this kind of biopharmaceutical system may be disposable, namely once the pouch contents have been used, the pouch is discarded and often the connecting tubes that were connected to it as well.

For this purpose, by way of an active illustrative example, a first connector 7a may be provided, male or female, connected to a flexible tube 93a which in turn is connected to the interior of the pouch 90. In this case, the connector 7a is provided with a tubular end piece capable of receiving and retaining a flexible tube 93; the first connector may be coupled to a second complementary connector 7b (male or female, of opposite gender to 7a), preferably with a non-permanent locking, meaning with the possibility of separating the two connectors once the filling of the pouch is completed, coupled to a tube 93b. Alternatively to this first solution, a second connector 7f fixed directly to the pouch 90 may be provided; in this case there are no longer any flexible tubes interposed between the connector and the pouch, but an attachment flange 80 is used that is fixed directly on the wall of the pouch 90 by gluing or welding.

In this alternative, an auxiliary connector denoted 7e, of the opposite gender and mounted on a flexible tube 93e, may be connected to this second connector, preferably with non-permanent locking, meaning with the possibility of separating the two connectors once the filling (phase "A") of the pouch is completed.

During the usage phase ("B"), a third connector 7c (male or female, of opposite gender to 7a and connected to tube 93c) is connected to the first connector 7a, to dispense the biopharmaceutical material toward the site of use. In this case, it may be necessary to ensure conditions of sterility during the usage phase, and it is therefore preferable to use a non-detachable connection.

In the variant shown on the left in FIG. 1, the third connector is denoted 7d (with its tube 93d), and it can form a non-detachable connection with the second connector 7f, preventing disconnection of the connectors 7a/7c.

It is therefore advantageous to provide connection solutions that are either removable or non-removable, in order to satisfy the various requirements of the configurations used in the field of biopharmaceutical applications.

In FIGS. 2 to 12, we will now describe in more detail the solutions proposed by the invention to satisfy the different requirements for removable or non-removable connections.

In the example shown, a female connector 1 is connected to a male connector 2 by a coupling movement in which the male connector is inserted into the female connector along an axial direction X.

For each of these connectors, in the present document the term "front" refers to the portion closest to the complementary mating connector, and the term "rear" means the part farthest from the complementary connector.

Figure 2:
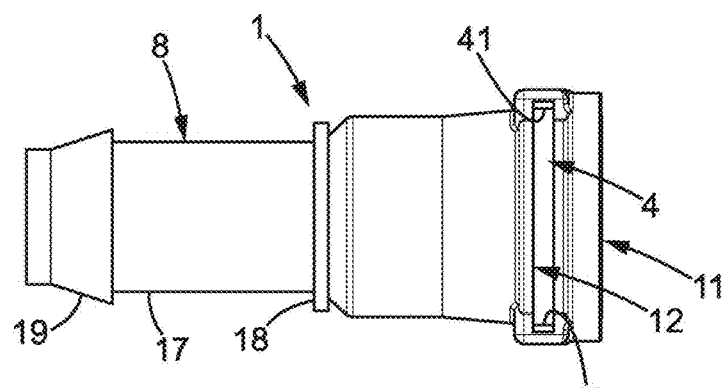
FIG. 2 shows a top view of the female connector without locking element, according to the invention.
Figure 3:
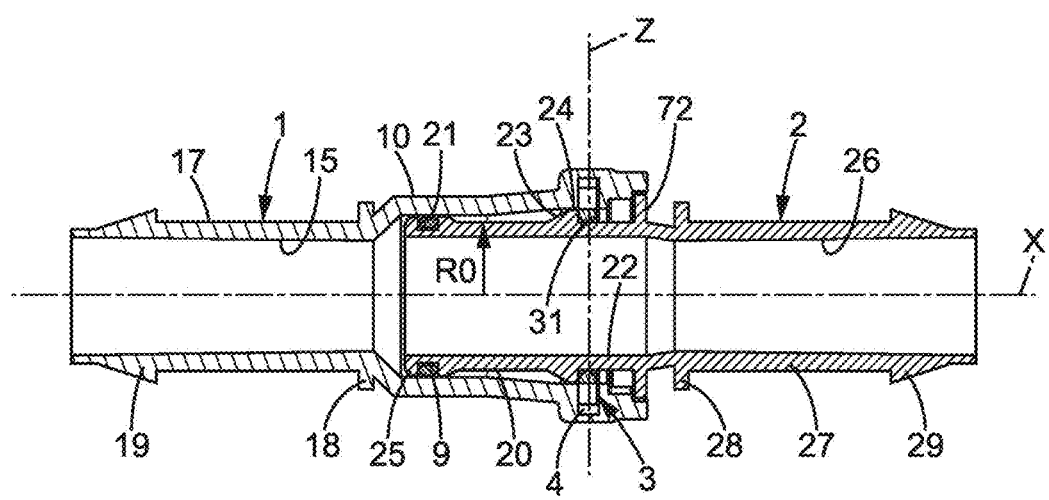
FIG. 3 is an axial sectional view of the connection device of FIG. 1, in the coupled position, along section line II-II shown in FIG. 5.
Figure 10:
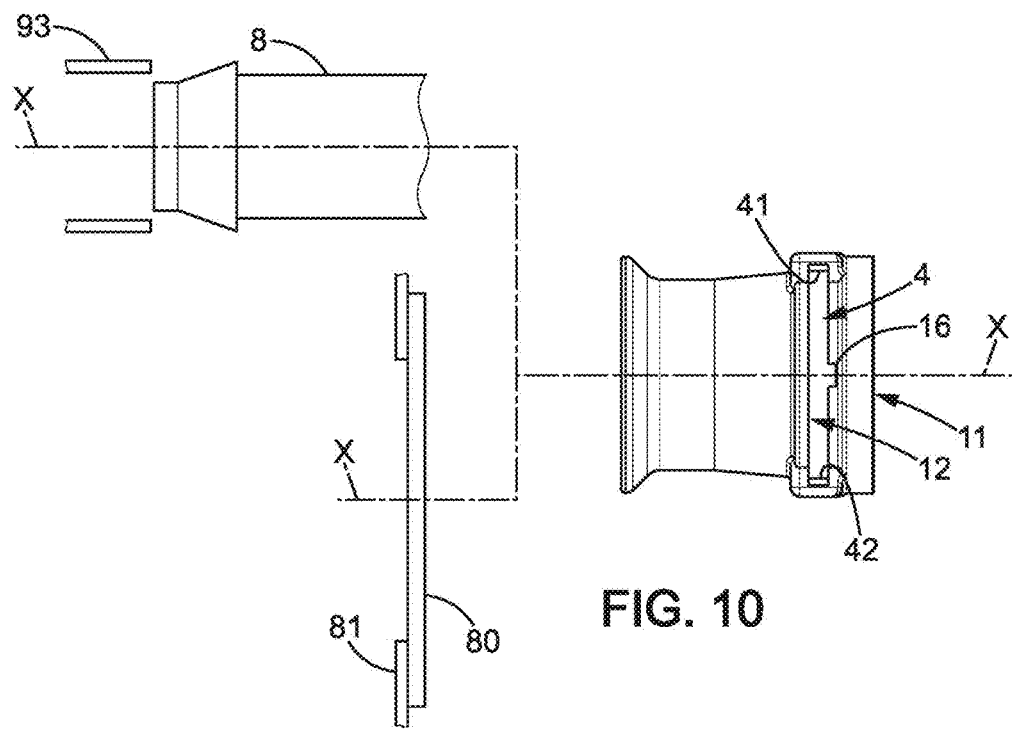
FIG. 10 shows a top view of the female connector without locking element and with foolproofing, with two possibilities for the rear portion.
Figure 11:
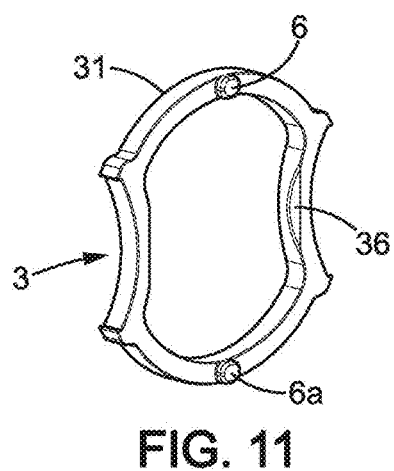
FIG. 11 is a perspective view of a locking ring with foolproofing.
Figure 12:
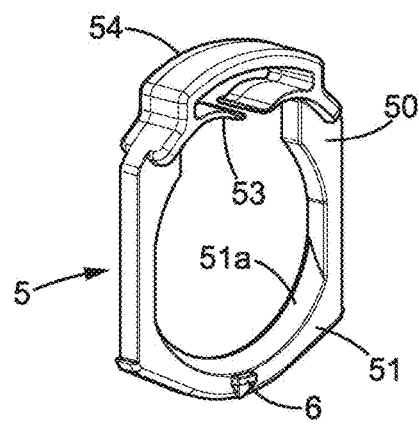
FIG. 12 is a perspective view of a locking slider with foolproofing.

In the example shown in FIGS. 2 and 3, the rear portion of each connector is formed by a tubular end piece 8,17 for receiving a flexible tube 93, such as those shown in FIGS. 1 and 10.

The female connector 1 comprises in its rear portion a tubular end piece 17 intended for receiving a flexible tube, and in its front portion an interface for coupling with the male connector 2; said coupling interface will be described below.

Similarly, the male connector 2 comprises in its rear portion a tubular end piece 27 intended for receiving a flexible tube, and in its front portion an interface for coupling with the female connector, which will be discussed further below.

It should be noted here that the female connector and/or the male connector could have, in their rear portions, instead of an end piece for receiving a tube as shown, a flange for connecting to a container such as a flexible or rigid pouch or a filter, for example.

Each of the tubular end pieces 17,27 is rotationally symmetrical about the X axis, and they each comprise one or more external retention catches 19,29 to retain the flexible tube, and a stop flange 18,28 which the flexible tube can abut against when it is inserted onto the end piece. As is known per se, a clamping collar may be added around the flexible tube and the end piece.

The male connector 2 comprises an axial passage 26 that is rotationally symmetrical about the X axis, which allows passage of the fluid being conveyed through the fluid coupling.

Starting from its front end portion, the male connector first comprises an entry chamfer 25, then an annular groove 21 for receiving a conventional O-ring 9, and a first intermediate portion 20 provided with longitudinal ribs, then a tapered portion 23 which flares outwardly and towards the rear of the male connector.

Still in the rearward direction of the connector, the tapered portion 23 is extended by an annular rim 24 which forms a shoulder intended to bear against a complementary surface and to prevent removal of the male connector as will be seen further below.

Behind the removal-preventing annular rim 24, the male connector comprises a second intermediate portion 22 with a ring 72 having four small reinforcements, said ring with reinforcements serving as gripping means for pushing the male connector towards the female connector and also serving as an axial stop for the insertion movement.

Behind the ring 72, there is the flange 28 and the tubular end piece 27 already described.

The female connector 1 comprises an axial passage 15 that is rotationally symmetrical about the X axis, allowing passage of the fluid conveyed through the fluid connection.

Starting from its rear end portion, the female connector 1 comprises the tubular end piece 17 already described, and a main body 10 for receiving the front portion of the male connector, with a bore of slightly larger diameter than the outer diameter of the front portion of the male end piece 2, to permit insertion of the front portion of the male connector and to be able to exert radial pressure on the O-ring 9 to ensure the sealing function.

Facing tapered portion 23, the body 10 has an inner dimension that increases until it reaches a housing 4 for a locking element which it will be discussed further below.

A housing 4 is provided in the front portion of the female connector, forming a slide extending in a transverse plane YZ perpendicular to the X axis. In the current case, the housing forming a slide is presented as a transverse slot. In addition, in the example illustrated, the slot is open at both sides in the transverse direction Z, which allows insertion of a locking ring.

In the example shown, the housing 4 comprises a first groove 41 and a second groove 42 which face each other and are arranged symmetrically with respect to the XZ plane.

Finally, the body 10 of the female connector comprises a front ring 11 which forms the front end and against which the ring 72 of the male connector will abut at the end of the insertion movement.

It should be noted here that it is not strictly necessary for the slot-like housing 4 to be open at both sides. In an alternative (not shown), one side may be at least partially closed which would form a bottom for the housing 4, while the opposite side would constitute the mouth through which the locking elements are inserted.

We will now describe the locking elements which functionally differentiate the connection, in other words they provide the choice of an unlockable locking element 5 and/or a non-unlockable locking element 3.

Figure 4:
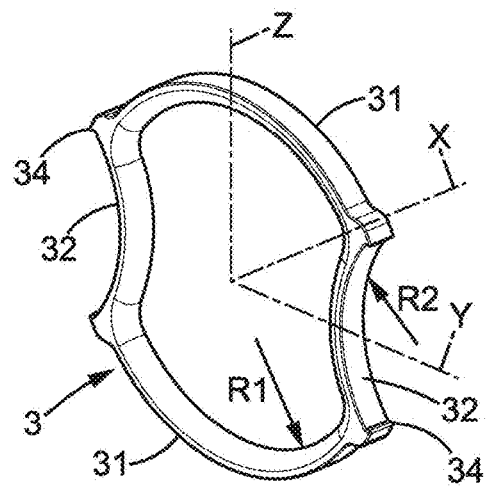
FIG. 4 is a perspective view of a deformable locking ring of the connection device of FIG. 3.
Figure 6:
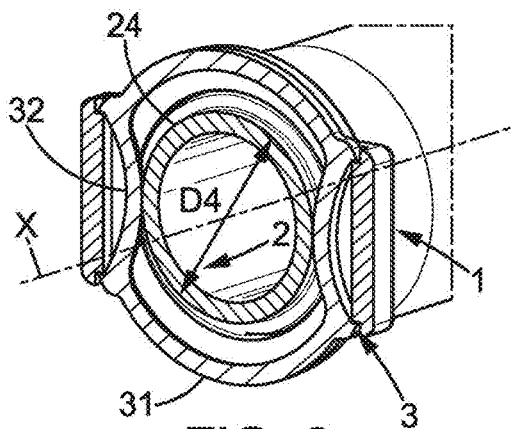
FIG. 6 shows a cross-section of the connection device of FIG. 3.
Figure 5:
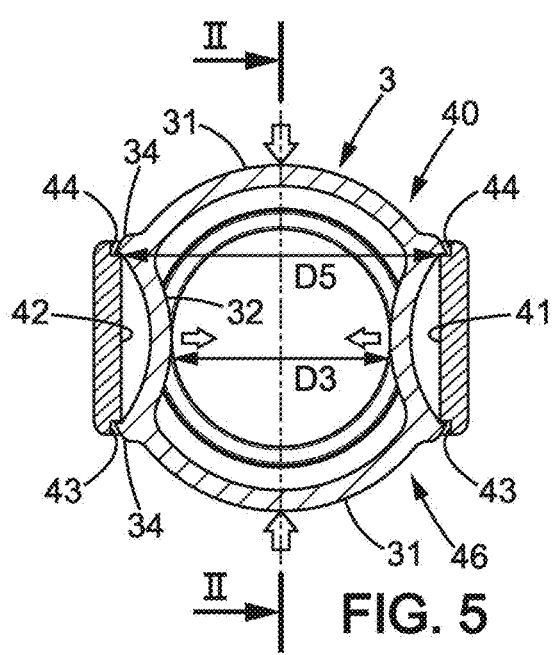
FIG. 5 is perspective view of a cross-section of the connection device of FIG. 3.
Figure 7:
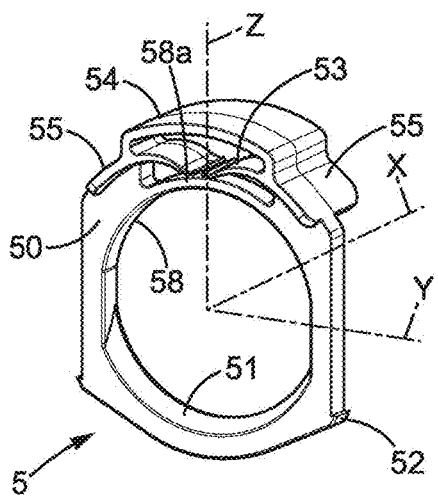
FIG. 7 is a perspective view of a locking slider.
Figure 9:
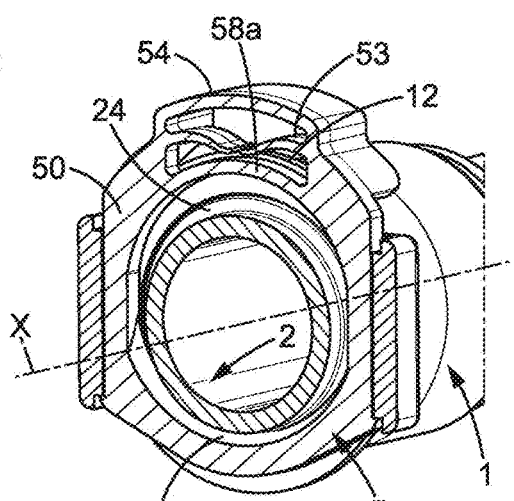
FIG. 9 is a perspective view of a cross-section of the connection device of FIG. 8.
Figure 8:
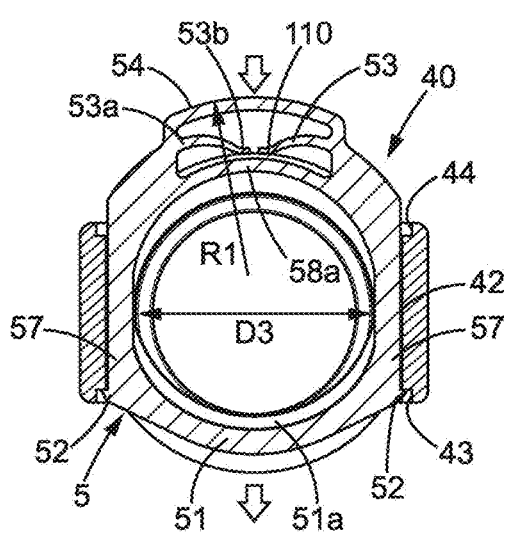
FIG. 8 shows a cross-section of the connection device with the locking slider of FIG. 7.

The non-releasable locking element 3 is formed by a deformable locking ring, as illustrated in FIGS. 4 to 6.

The locking ring 3 already mentioned is intended to be inserted into the housing 4 of the body of the female connector. The locking ring 3 is formed as a closed deformable ring, meaning that it can be deformed radially outward during the movement of inserting the male connector into the female connector.

More specifically, the locking ring comprises two diametrically opposed first arched portions 31, concave as viewed from the X axis, and two diametrically opposed second arched portions 32 of inverse curvature, meaning convex as viewed from the axis, each of the second arched portions being interposed between two first arched portions. In other words, when traveling along the ring circumferentially, one encounters a first arched portion, then a second arched portion of inverse curvature, then another first arched portion, and finally another second arched portion of reverse curvature.

The first arched portions 31 are concave as viewed from the X axis, meaning that their curvature is directed toward the inside of the ring, while the second arched portions 32 are convex as viewed from the X axis, meaning that their curvature is directed toward the outside of the ring.

Advantageously, each of the first arched portions 31 here form an arc centered on the X axis, with a first radius of curvature R1 (FIG. 4) of between 100% and 200% of the radius R0 of the male connector, and the second arched portions 32 each form an arc with a second radius of curvature R2 of between 70% and 130% of the first radius of curvature R1.

The second arched portions 32 are adapted to flex outwardly during insertion of the male connector, in particular when the tapered shape 23 presses on the ring. After complete insertion of the male connector, the external annular rim 24 has passed beyond the ring, and the ring is returned to its rest position and then abuts against the retaining external annular rim 24 to prevent removal of the male connector.

When the locking ring 3 is at rest, the distance D3 (FIGS. 5 and 6) between the two second arched portions is slightly smaller than the diameter D4 of the second intermediate portion 22 of the male connector behind the annular rim 24.

Note that the second arched portions 32 are inaccessible from the outside when the deformable ring is in position in the housing 4, and only the first arched portions 31 remain accessible; but, as is illustrated in FIG. 5, a radial inward pressure tends to accentuate the curvature of the second arched portions and therefore tends to reinforce the locking, so that it is impossible to unlock the connection, even unintentionally or if dropped or if the connector strikes an object.

Prior to insertion of the male connector, the locking ring 3 can be maintained in a "standby" position within the housing, by various means. In the example shown, the locking ring is held in the housing by projections 34, arranged substantially where the first arched portions meet the second arched portions, providing four projections 34 which could also be called hooks, catches, or claws. Said projections 34 extend outwardly generally in the Y direction. Corresponding facing recesses 43,44 are provided in the grooves 41, 42, these recesses being intended to receive the projections of the locking ring when the latter reaches its position substantially centered on the X axis.

Advantageously, the flexibility properties of the ring are used not only for coupling the male connector in the female connector, but also for the prior insertion of the locking ring 3 in the slot 4 along direction Z. More specifically, the distance along Y between the ends of the projections 34 is slightly greater than the distance D5 between the bottoms of the grooves 41, 42. Thus, during insertion, the projections 34 are compressed slightly inward in order to slide along each of the grooves 41,42, and return to the rest position once the projections 34 are facing said recesses 43,44. Precise positioning of the ring is not necessarily required: there can be some play as long as the ring is approximately centered on the X axis.

The releasable locking element 5 is formed by a part which is referred to hereinafter as a locking slider 5.

The locking slider 5, already mentioned, is intended to be inserted into said housing 4 of the body of the female connector. The locking slider 5 is formed as a molded plastic part comprising a locking plate 50, arranged transversely to the X axis, with a central opening 58 through which the male connector 2 can pass. The locking plate 50 has two parallel lateral portions 57 respectively engaged in the grooves 41,42.

In addition, the locking slider 5 comprises an actuation pushbutton 54 integrally formed with the plate, configured to be pushed toward the axis to unlock the connection, by recentering the axial opening 58.

In addition, the locking slider 5 comprises two flexible tabs 53 formed integrally with the slider, the flexible tabs returning the slider toward the first position, referred to as the locking position. The two flexible tabs 53 are adapted to flex to allow the locking plate 50 to move to the second position, referred to as the unlocking position.

Advantageously, the two flexible tabs 53 are arranged symmetrically with respect to the XZ plane. In addition, the flexible tabs are arranged under the actuation pushbutton 54. Preferably, they are interposed between the activation pushbutton 54 and a top edge 58a of the main opening 58. In addition, one will note that each of the flexible tabs 53 has a curvature directed away from the pushbutton, in other words curving downwards. In addition, each of the flexible tabs 53 preferably has a cross-section which decreases from its root 53a to its free end 53b.

The body 10 has a front ring 11 and a rear ring 12, already mentioned, in the housing area, which surround the housing. The mouth 40 is interposed between a front edge 110 of the front ring 11 and a rear edge of the rear ring 12; the flexible tab 53 presses on both the front edge 110 and the rear edge.

It should be noted here that instead of having multiple flexible tabs, there could be a single flexible tab 53 pressing on the body of the female connector on each side of the mouth, with the same advantages.

Prior to insertion of the male connector, the locking slider 5 can be maintained in a standby position within the housing by various means. In the illustrated example, the locking slider 5 is held in the housing by projections 52, arranged substantially at the lower ends (opposite the position of the pushbutton) of the lateral portions 57 of the locking plate. The two projections 52, which could also be called hooks, catches, or claws, extend outward generally in the Y direction. Facing recesses 43 are provided at the ends of the grooves 41, 42 of the housing, these recesses, in particular those denoted 43, being intended to receive the projections of the slider 52 when said slider reaches the position where the axial opening 58 is substantially centered on the X axis.

The flexibility of the slider 5 and of the projections 52 allows, prior to coupling the male connector within the female connector, inserting the locking slider along the Z direction from the upper mouth 40 of the housing.

Once the slider is installed in the housing, these projections 52 prevent its upward removal: it can only be pushed downward by means of the activation pushbutton 54.

Advantageously, the lower retaining portion 51 comprises a ramp shape 51a, in other words a bevel, intended to facilitate the insertion movement of the male connector which must move the slider downward until the retaining annular rim 24 has passed beyond the retaining portion 51, which then causes the slider to rise due to the return forces of the flexible tabs 53.

The female connector 1 and the male connector 2 may be obtained by molding a first plastic material, in particular plastic materials biocompatible with the various biopharmaceutical substances, for example polypropylene, polyethylene, polycarbonate, polysulfone, polyvinylidene chloride, polyethyleneimine. Preferably, polyethylene or polypropylene is chosen.

The deformable locking ring 3 and the locking slider 5 may be also made of the same material, for example polybutylene terephthalate, polypropylene, polyethylene, polycarbonate, polyoxymethylene; alternatively, and advantageously in some cases, a second plastic material different from that of the connectors may be chosen for the deformable ring 3, typically polybutylene terephthalate or polycarbonate, with more targeted mechanical and elastic properties, as the locking ring is never in contact with the substances conveyed in the pipe to be connected.

Similarly, a second different plastic material or even a third plastic material may be chosen for the slider 5, with mechanical and elastic properties more suitable for optimizing the flexible tabs, as the locking slider is never in contact with the substances conveyed in the pipe to be connected.

For the flexible tabs of the slider, and for the arched portions of the deformable locking ring, one can optimize the compromise between stiffness and elasticity of the second material. One can also take into account the changing properties of the material due to natural aging or caused by light or other radiation, or other physico-chemical exposure.

FIG. 10 illustrates the fact that each of the female connector 1 and the male connector 2 (not shown) may be interfaced with a flexible tube 93, or directly with the pouch 90 or container by means of the attachment flange 80 which can be sealingly fixed around an opening in the wall 81 of the pouch by welding, coupling, or another suitable alternative.

In addition, for the foolproofing function, the front wall of the slot-like housing 4 is provided with a notch 16, which makes the housing asymmetrical in the YZ plane, foolproofing the direction of insertion of the deformable ring and/or the slider.

Correspondingly, the deformable ring 3 comprises at least one pin 6 arranged in the middle of a first arched portion 31, protruding in the axial direction X, such that it will enter said notch 16. Advantageously, two pins 6,6A may be provided, one on each of the first arched portions on the front face of the deformable ring, meaning on the face where the beveled face 36 is located.

As for the slider 5 (FIG. 12), a pin 6 arranged in the middle of the retaining portion 51 on the front face 50 of the locking plate of the slider is similarly provided, meaning on the face where the beveled face 51a is located.

Advantageously in the context of the invention, it is also possible to have "double female" connections, which have a female connector on each side providing a housing into which either a deformable ring or a slider can be inserted.

The modular principle described above may also be used in combination with aseptic connectors provided with a sterile membrane.

Note that in the example illustrated, the male connector may rotate about X within the female connector: there is no particular orientation for inserting the male connector into the female connector.

However, it is not excluded to provide an anti-rotation device which may, for example, be arranged between the small reinforcements of the ring 72 of the male connector and the front ring 11 of the female connector.

The invention claimed is:

1. An assembly comprising a female connector for fluid connection, adapted for receiving a male connector having a retaining external annular rim, the female connector comprising a body with a bore of axis X, and a housing forming a slide extending generally within a transverse plane YZ perpendicular to the axis X, the housing comprising two parallel lateral grooves and the housing being open at least at one of its ends in a sliding direction Z of the slide, the assembly further comprising:
a non-unlockable locking element, in the form of a deformable locking ring formed as one piece and adapted to be inserted into the housing and to lock the male connector in a coupling position, with no possibility of unlocking by a user operation,
an unlockable locking element made separate from the non-unlockable locking element and structurally different from the non-unlockable locking element, the unlockable locking element being in the form of a locking slider adapted to be inserted into the housing and movable between a locking position and a unlocking position, the locking slider comprising a locking plate with a central opening through which the male connector can pass, and an actuation pushbutton integrally formed with the locking plate, configured to be pushed toward the axis X in order to unlock the connection,
wherein the female connector is configured to receive:
either the non-unlockable locking element;
or the unlockable locking element,
so that only one determined locking element indiscriminately chosen amongst said non-unlockable locking element and said unlockable locking element is inserted into the housing in an operational state of the assembly where the retaining external annular rim of the male connector is engaged by the determined locking element.

2. The assembly according to claim 1, wherein the locking slider and the deformable locking ring are asymmetrical with respect to the transverse plane YZ, with the front side of the deformable locking ring and the front side of the locking slider respectively having a bevel shape.

3. The assembly according to claim 2, wherein the housing is asymmetrical with respect to the transverse plane YZ, the locking slider and the deformable locking ring each comprising at least one projecting pin designed to engage with at least one corresponding notch in the housing.

4. The assembly according to claim 1, wherein the housing is open at both ends along Z and is symmetrical with respect to the XY plane, so that it is possible to insert the locking slider and the deformable locking ring indiscriminately from either side of the housing.

5. The assembly according to claim 1, wherein the locking slider has a double symmetry, with respect to planes XZ and YZ.

6. The assembly according to claim 1, wherein the deformable locking ring has a triple symmetry, with respect to planes XZ, YZ, and XY.

7. The assembly according to claim 1, wherein the body of the female connector is made of a first biocompatible plastic material, the deformable locking ring is made of a second plastic material, and the locking slider is made of the second plastic material or of a third plastic material.

8. The assembly according to claim 1, wherein the two parallel lateral grooves of the housing comprise at least one recess configured to indiscriminately accommodate projections that are respectively part of either the deformable locking ring or the locking slider.

9. The assembly according to claim 8, wherein the housing comprises recesses arranged in pairs, symmetrically with respect to the XY plane, so as to accommodate the deformable locking ring and/or the locking slider regardless of the end of the housing through which they are inserted.

10. The assembly according to claim 1, wherein the deformable locking ring comprises two diametrically opposed first arched portions, concave as viewed from the axis X, and two diametrically opposed second arched portions of inverse curvature, meaning convex as viewed from the axis X, each of said second arched portions being interposed between two first arched portions, whereby definitive locking is obtained after the male connector is locked in the female connector: it is no longer being possible to unlock the connection by manipulation or pressure on the deformable locking ring, as the second arched portions are not directly accessible and the second arched portions tend to reinforce the lock in case of applied force or impact.

11. The assembly according to claim 1, wherein the locking slider comprises at least one flexible tab integrally formed with the locking slider, the flexible tab returning the locking slider toward the locking position of the locking slider and able to flex to allow the locking plate to move toward the second position, the flexible tab being configured to press on each side of the mouth of the housing in the axial direction X.

12. The assembly according to claim 1, further comprising in its rear portion a tubular end piece for receiving and retaining a flexible tube.

13. The assembly according to claim 1, further comprising in its rear portion an attachment flange configured to be sealingly fixed to the wall of a container or pouch.

14. The assembly according to claim 10, wherein the locking slider comprises two lateral portions extending rectilinearly along the sliding direction Z of the slide when the locking slider is inserted in the housing.

15. An assembly comprising a female connector for fluid connection and two additional pieces, the assembly being adapted for receiving a male connector having a retaining external annular rim,
wherein the female connector comprises a body extending annularly around a longitudinal axis, and a housing forming a slide extending generally within a transverse plane perpendicular to the longitudinal axis, the body comprising a front ring and a rear ring, the housing comprising two parallel lateral grooves and the housing having an outer mouth delimited between a front edge included in the front ring and a rear edge included in the rear ring,
the two additional pieces being:
a deformable locking ring, which is a non-unlockable, formed as one piece and adapted to be inserted into the housing and to lock the male connector in a coupling position, with no possibility of unlocking by a user operation as the deformable locking ring is in a definitively inserted position, and
a locking slider, made separate and structurally different from the deformable locking ring, made as one piece and adapted to be inserted into the housing and movable between a locking position and a unlocking position, the locking slider comprising a locking plate with a central opening through which the male connector can pass, and an actuation pushbutton integrally formed with the locking plate, configured to be pushed toward the longitudinal axis in order to unlock the connection,
wherein the female connector is configured to receive:
the deformable locking ring, while the locking slider is kept outside the housing and not used to form the connection; and
the locking slider, while the deformable locking ring is kept outside the housing and not used to form the connection.

16. The assembly according to claim 15, wherein the body of the female connector is made of a first biocompatible plastic material, the deformable locking ring is made of a second plastic material, and the locking slider is made of the second plastic material or of a third plastic material.

17. The assembly according to claim 15, wherein the two parallel lateral grooves of the housing comprise at least one recess,
and wherein the deformable locking ring and the locking slider have each projections, protruding radially outward, adapted to be accommodated in the at least one recess.

18. The assembly according to claim 15, wherein, in the definitively inserted position:
the deformable locking ring comprises two diametrically opposed first arched portions, concave as viewed from the longitudinal axis, and two diametrically opposed second arched portions of inverse curvature, meaning convex as viewed from the longitudinal axis, each of said second arched portions being interposed between two first arched portions, the second arched portions being not directly accessible from outside the housing.

19. The assembly according to claim 15, wherein the locking slider comprises at least one flexible tab integrally formed with the locking slider, the flexible tab returning the locking slider toward the locking position and able to flex to allow the locking plate to move toward the unlocking position, the flexible tab being configured to press on both the front edge and the rear edge.

20. An assembly comprising a female connector for fluid connection and two additional pieces, the assembly being adapted for receiving a male connector having a retaining external annular rim,
wherein the female connector comprises a body extending annularly around a longitudinal axis, and a housing forming a slide extending generally within a transverse plane perpendicular to the longitudinal axis, the housing comprising two parallel lateral grooves and being open at a mouth opening radially outside in a sliding direction of the slide, the sliding direction being perpendicular to the longitudinal axis,
the two additional pieces being:
a deformable locking ring, which is a non-unlockable, formed as one piece and adapted to be inserted into the housing and to lock the male connector in a coupling position, with no possibility of unlocking by a user operation as the deformable locking ring is in a definitively inserted position, and
a locking slider, made separate and structurally different from the deformable locking ring, made as one piece and adapted to be inserted into the housing and movable between a locking position and a unlocking position, the locking slider comprising a locking plate with a central opening through which the male connector can pass, and an actuation pushbutton integrally formed with the locking plate, configured to be pushed toward the longitudinal axis in order to unlock the connection,
wherein the female connector is configured to receive:
the deformable locking ring, while the locking slider is kept outside the housing and not used to form the connection; and
the locking slider, while the deformable locking ring is kept outside the housing and not used to form the connection,
and wherein the deformable locking ring has three distinct symmetry planes that are perpendicular to each other, one of the three symmetry planes corresponding to a sliding plane transverse to the longitudinal axis in the definitively inserted position.

\* \* \* \* \*